(12) United States Patent
Tuseth

(10) Patent No.: US 9,539,378 B2
(45) Date of Patent: Jan. 10, 2017

(54) PERCUTANEOUS SYSTEM, DEVICES AND METHODS

(71) Applicant: DAassist AS, Bergen (NO)

(72) Inventor: Vegard Tuseth, Bergen (NO)

(73) Assignee: NUHEART AS, Bergen (NO)

( * ) Notice: Subject to any disclaimer, the term of this patent is extended or adjusted under 35 U.S.C. 154(b) by 118 days.

(21) Appl. No.: 14/335,142

(22) Filed: Jul. 18, 2014

(65) Prior Publication Data

US 2015/0258312 A1 Sep. 17, 2015

(30) Foreign Application Priority Data

Mar. 17, 2014 (NO) .................................... 20140353
Jun. 10, 2014 (GB) .................................... 1410320.4

(51) Int. Cl.
| | | |
|---|---|---|
| *A61M 1/10* | (2006.01) | |
| *A61M 1/12* | (2006.01) | |
| *A61B 17/11* | (2006.01) | |
| *A61B 17/34* | (2006.01) | |
| *A61M 27/00* | (2006.01) | |

(Continued)

(52) U.S. Cl.
CPC ............. *A61M 1/1008* (2014.02); *A61B 17/11* (2013.01); *A61B 17/3468* (2013.01); *A61B 17/3478* (2013.01); *A61M 1/101* (2013.01); *A61M 1/122* (2014.02); *A61M 1/125* (2014.02); *A61M 27/002* (2013.01); *A61M 29/00* (2013.01); *A61B 2017/00243* (2013.01); *A61B 2017/00247* (2013.01); *A61B 2017/00252* (2013.01); *A61B 2017/00685* (2013.01); *A61B 2017/00867* (2013.01); *A61B 2017/00876* (2013.01); *A61B 2017/1107* (2013.01); *A61B 2017/1139* (2013.01); *A61B 2017/3488* (2013.01); *A61M 27/006* (2013.01)

(58) Field of Classification Search
CPC ................. A61B 17/11; A61B 17/3468; A61B 2017/1107; A61M 1/1008; A61M 1/101; A61M 1/122; A61M 1/125; A61M 27/002; A61M 27/006
See application file for complete search history.

(56) References Cited

U.S. PATENT DOCUMENTS

| 5,921,913 A | 7/1999 | Siess |
|---|---|---|
| 7,878,967 B1 | 2/2011 | Khanal |

(Continued)

FOREIGN PATENT DOCUMENTS

| EP | 2 338 540 A1 | 6/2011 |
|---|---|---|
| GB | 2504176 A | 1/2014 |

(Continued)

OTHER PUBLICATIONS

International Search Report and Written Opinion in International Application No. PCT/EP2015/055578, dated Oct. 29, 2015.

*Primary Examiner* — Tatyana Zalukaeva
*Assistant Examiner* — Benjamin Klein
(74) *Attorney, Agent, or Firm* — Baker & Hostetler LLP

(57) ABSTRACT

A percutaneous system, method and related devices are provided. More particularly, a percutaneous system comprises one or more of an intracorporeal connector for fluid communication between two anatomical compartments, through an anatomical wall, an intracorporeal device for regulating the flow of fluid between the two anatomical compartments, and a percutaneous insertion device.

12 Claims, 19 Drawing Sheets

(51) Int. Cl.
*A61M 29/00* (2006.01)
*A61B 17/00* (2006.01)

(56) References Cited

U.S. PATENT DOCUMENTS

| | | | |
|---|---|---|---|
| 7,942,804 B2* | 5/2011 | Khaw | 600/16 |
| 2002/0173742 A1 | 11/2002 | Keren et al. | |
| 2003/0100920 A1 | 5/2003 | Akin et al. | |
| 2003/0233143 A1 | 12/2003 | Gharib et al. | |
| 2004/0236170 A1 | 11/2004 | Kim | |
| 2004/0243051 A1* | 12/2004 | Monzyk et al. | 604/6.08 |
| 2005/0165344 A1 | 7/2005 | Dobak, III | |
| 2005/0187425 A1 | 8/2005 | Alferness et al. | |
| 2006/0089707 A1 | 4/2006 | Vassiliades et al. | |
| 2007/0249985 A1* | 10/2007 | Brenneman | A61B 17/083 604/8 |
| 2009/0088597 A1* | 4/2009 | Frazier et al. | 600/16 |
| 2009/0093751 A1* | 4/2009 | Tao et al. | 604/23 |
| 2009/0182188 A1 | 7/2009 | Marseille et al. | |
| 2010/0191035 A1 | 7/2010 | Kang et al. | |
| 2011/0130619 A1* | 6/2011 | Whisenant et al. | 600/16 |
| 2011/0196190 A1* | 8/2011 | Farnan et al. | 600/16 |
| 2011/0306916 A1 | 12/2011 | Nitzan et al. | |
| 2012/0165928 A1 | 6/2012 | Nitzan et al. | |
| 2012/0172654 A1* | 7/2012 | Bates | 600/16 |
| 2012/0178985 A1 | 7/2012 | Walters et al. | |
| 2014/0336445 A1 | 11/2014 | Farnan et al. | |
| 2015/0250935 A1* | 9/2015 | Anderson et al. | 600/16 |

FOREIGN PATENT DOCUMENTS

| | | |
|---|---|---|
| WO | 00/27312 A1 | 5/2000 |
| WO | WO 0178580 A2 * | 10/2001 |
| WO | 2007/003351 A1 | 1/2007 |
| WO | 2008/027869 A2 | 3/2008 |
| WO | WO2008055301 A1 | 5/2008 |
| WO | 2013/036588 A1 | 3/2013 |
| WO | 2015/075576 A1 | 5/2015 |

* cited by examiner

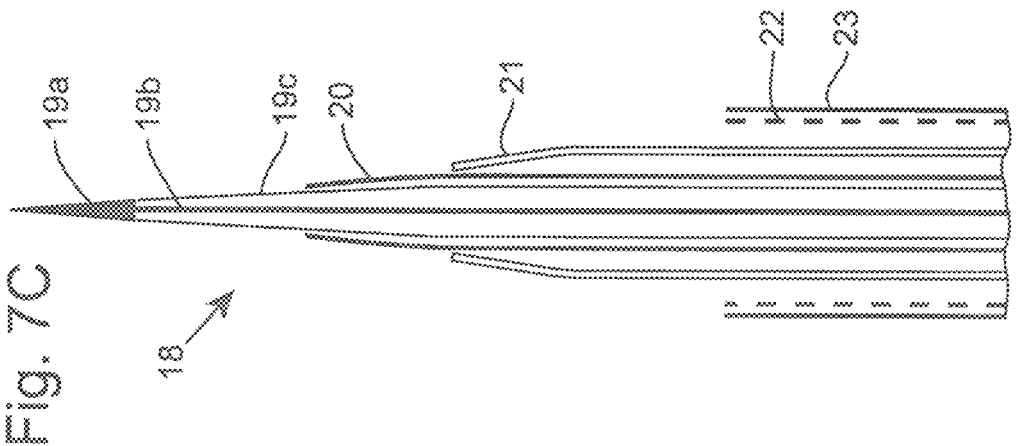
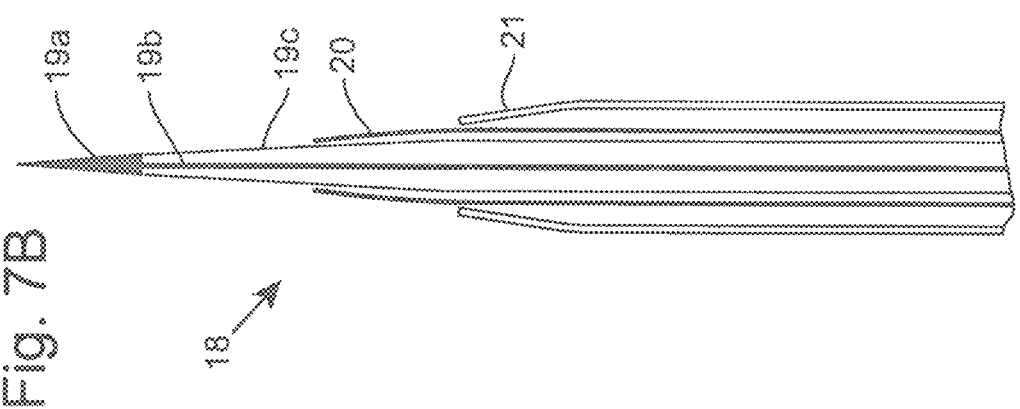
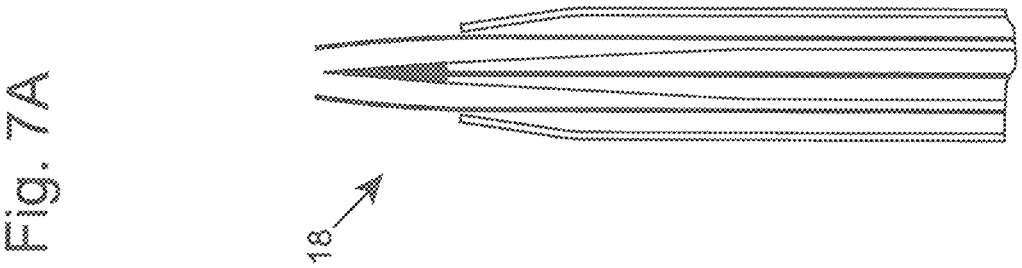

Fig. 16
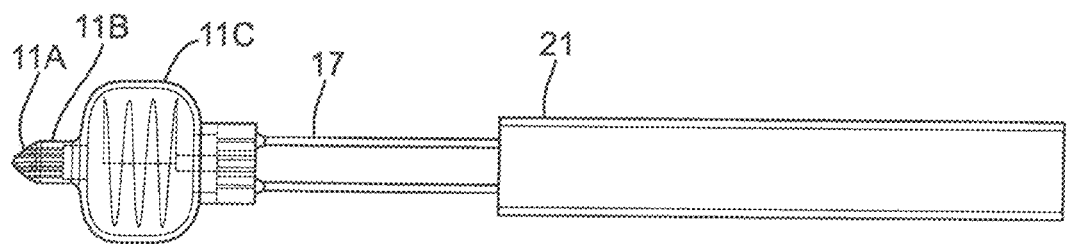
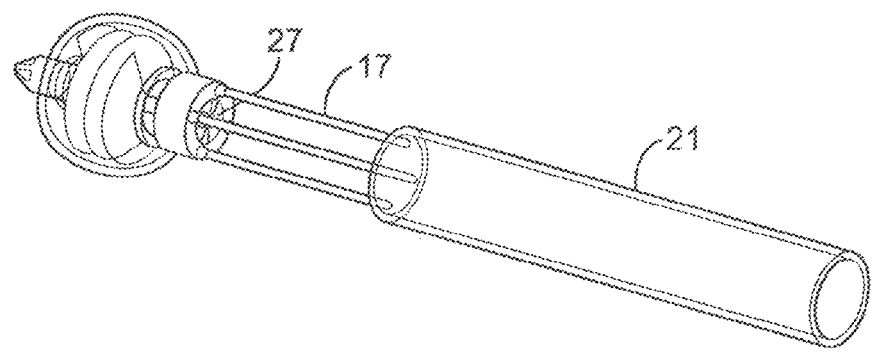
Fig. 17
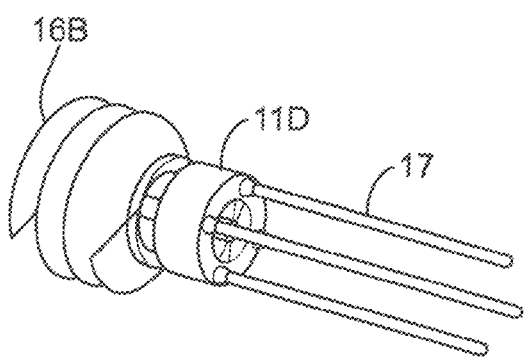
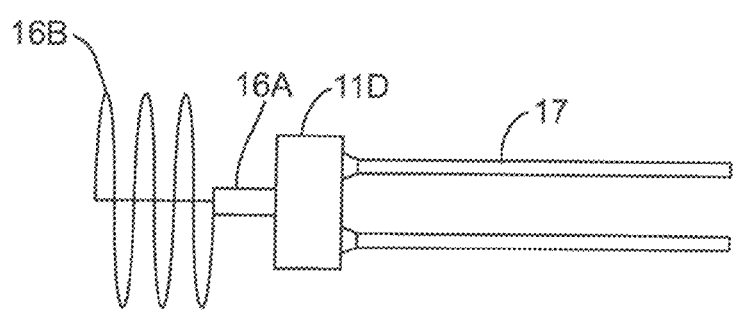

PERCUTANEOUS SYSTEM, DEVICES AND METHODS

CROSS-REFERENCE TO RELATED APPLICATIONS

This application claims priority to foreign Norwegian patent application NO 20140353 filed on Mar. 17, 2014, and United Kingdom patent application GB 1410320.4 filed on Jun. 10, 2014, the disclosures of which are incorporated by reference in their entireties.

FIELD OF THE INVENTION

The present invention generally relates to the field of medical devices and surgery devices. More specifically, the present invention relates to a percutaneous system and corresponding devices and methods of treatment. The present invention is particularly useful as a mechanical circulatory support system for example for the treatment of circulatory collapse, heart failure and heart conditions requiring a circulatory assist device but also has a wider variety of applications.

BACKGROUND

Examples of mechanical circulatory support systems (MCS) include ventricular assist devices (VADs). A VAD is a mechanical pumping device capable of supporting heart function and blood flow. Specifically, a VAD helps one or both ventricles of the heart to pump blood trough the circulatory system. Left ventricular assist devices (LVAD), right ventricular assist devices (RVAD) and biventricular assist devices (BiVAD) are currently available. Also, circulatory support systems may include cardiopulmonary support (CPS, ECMO), which provide means for blood oxygenation as well as blood pumping. Such devices may be required during, before and/or after heart surgery or to treat severe heart conditions such as heart failure, cardiopulmonary arrest (CPA), ventricular arrhythmia or cardiogenic shock.

Traditionally, VADs are fitted during open-heart surgery through an incision in the chest and the procedure involves puncturing the apex of the left ventricle to re-route blood from the ventricle to the aorta through an external pump. An example of device used in surgical VAD is HeartMate II™. Such surgical procedures are clearly invasive and unsuitable for weaker and vulnerable patients as they involve a greater recovery time and carry the risks of infection and trauma. This particularly the case in the treatment of children for whom existing surgical equipments and devices are comparatively bulkier and more invasive, and a reduction of the size of the equipment is often difficult if not impossible in view of the equipment and procedure involved. Furthermore, these devices require the intervention from a team of skilled surgical staff in a hospital environment and are therefore less available and costly.

More recent procedures are non-surgical and involve the insertion of a VAD through a small incision made at the groin of the patient. A popular version of such so-called percutaneous VAD is the TandemHeart™ device. A tube is introduced trough an incision adjacent the groin of the patient and advanced along the femoral vein and inferior vena cava, across the intra-atrial septum and into the left atrium so that oxygenated blood from the left atrium is fed into a pumping device located outside the patient's body and recirculated through an outflow tube into the femoral artery. Although this device has shown promising results, it only provides short-term support (up to two weeks) and is unsuitable for long-term treatments. The external pump is bulky and requires patient's immobilization for as long as the device is fitted. Furthermore, there is a risk of life-threatening infection around the groin incision, which remains open during the treatment, and of considerable bleeding from a major artery. In addition, the tube of the TandemHeart™ ends in the left atrium from which blood is pumped out and led outside the patient's body. This type of blood inlet system can potentially become hindered, if not blocked, if surrounding tissues are accidentally sucked in, thereby resulting to a loss of efficiency.

Another popular percutaneous VAD is the Impella™ device, which is inserted into the femoral artery and descending aorta. The Impella™ device comprises an elongated end, which is implanted across the natural aortic valve, with a blood inlet placed in the left ventricle and a blood outlet above the aortic valve. A pump circulates blood from the inlet to the outlet. The driveline is externalised through the femoral artery during use and the same limitations apply as with TandemHeart™ and other current percutaneous MCS systems. This device is approved to provide support for up to a week. There is therefore a need for a device with reduced risk of infection and bleeding and increased mechanical stability which can be used as part of a short-term "bridge to recovery" treatment or as a long-term treatment including patient mobilisation. In addition, the efficiency of the pump is limited because it is not possible to insert a pump of the size required to provide a suitable blood flow using percutaneous arterial access. Presently, the problem of limited pump capacity and duration with percutaneous MCS is solved either by inserting larger intracorporeal pumps surgically or by choosing an extracorporeal pump, with all the potential problems are described above.

Known mechanical circulatory support systems are life-saving. However, they remain costly, complex and have limited clinical potential with a majority of patients still passing away unaided.

Currently available percutaneous treatments rely on the main structures of the patient's anatomical vascular structure to be undamaged. However, many heart patients are children with congenital heart defects or elderly patients often with anatomical and vascular anomalies, such as calcifications and valvular disease. With surgery, such limitations may be overcome but benefit is hampered by the risk associated with surgical trauma. There is therefore a need for a procedure and device that can safely and predictably be deployed by percutaneously achieving access from one anatomical structure to another as this will allow for safe delivery of more efficient pumps without surgical trauma.

SUMMARY OF THE INVENTION

It is an object of this invention to mitigate problems such as those described above.

According to a first aspect of the invention, there is provided a percutaneous system comprising an intracorporeal connector for fluid communication between two anatomical compartments through at least one anatomical wall.

The system according to the present invention is percutaneous and there is therefore no need for invasive and traumatic open surgery (as required for example to install a HeartMate™ system). Furthermore, the connector is intracorporeal so that no major external parts are required. There is no need for complete patient immobilisation, as it is the case with a TandemHeart™ system, in which an extracorporeal pump is required. The system can therefore be used for short-, medium- and long term treatment. In addition, by connecting two anatomical compartments through one or more anatomical walls, the system can by-pass defective or anomalous anatomical parts. Rather than fixing or replacing existing problematic anatomical parts, the system according to the present invention effectively creates a new pathway for fluid circulation. This is therefore the basis for a more forgiving and versatile procedure.

The present invention is particularly advantageous when one or both compartments are compartments of the circulatory system. Alternatively or additionally, one or both compartments are compartments within the thoracic cavity or the abdomen.

Preferably, the at least one anatomical wall is an outer wall of the compartment. For example, where the treatment is applied to the heart, then the artificial fluid passageway is an extra-cardiac passageway. Within the context of the invention, the expression "extra-cardiac passageway" means between the inside of the heart and the outside of the heart.

Preferably, the connector connects two adjacent compartments. The number of walls through which fluid communication is created depends on the compartments to be connected. For example, a left atrium to aorta connection involves puncture and fluid communication through two anatomical walls (i.e. the roof of the left atrium and the aortic wall), whereas a right to left atrium connection only involves one anatomical wall (i.e. the atrial septum). Fluid communication is established through internal anatomical walls and not through external walls such as skin tissues.

Preferably, the connector comprises a neck for fluid passage from one compartment to the other and means for securing the neck across the anatomical wall. In use, the neck of the connector is preferably embedded across the anatomical wall(s) and, if applicable, across interstitial space between two anatomical compartments/walls. An embodiment of the neck may comprise a channel for fluid passage from one compartment to the other. The neck portion is preferably sealed so that there is no fluid lateral leakage into the anatomical wall(s) and/or into any space separating two anatomical walls.

The neck can be susceptible to be dislodged, not only from the patient's movement, but also from the heart beating mechanism itself and it is therefore preferable to include means for securing and/or anchoring the neck across the anatomical wall(s). Thus, the securing means may comprise an anchor extending from a first end of the neck. The anchor may be expandable. More preferably, in its securing position, the anchor lies substantially parallel to the anatomical wall. In a preferred embodiment, the anchor can extend substantially perpendicularly from a first end of the neck and lay substantially parallel to the anatomical wall. Preferably, the anchor will be located in the anatomical compartment into which the fluid is delivered.

Preferably, the connector comprises means for preventing tissue from hindering fluid passage through the neck. The fluid passage, in particular in the case where a pumping device is used, creates a suction of the surrounding tissues towards the connector neck. The prevention means may comprise a shield extending from a second end of the neck. The shield may be expandable. The shield prevents surrounding tissues from becoming trapped in the connector neck and from hindering fluid passage. This type of shield can also act as an additional means for securing the connector neck in its correct position. Preferably, the shield is located in the anatomical compartment from which the fluid is removed. Preferably, the shield in its expanded state does not substantially contact the anatomical wall. This embodiment is advantageous in that the surrounding tissues do not rub directly against the shield and are not sucked into the shield, so that scratches and injuries can therefore be avoided. Mesh-type or grid-type materials are preferred so as to minimise the amount of foreign material introduced into the patient.

In a preferred embodiment, the connector is made wholly or partly of a shape memory material. The non-expanded connector can therefore fit into a sheath for percutaneous introduction into the patient. Preferably, the anchor and/or the shield are made of shape memory material. The connector can be introduced in a non-expanded elongated state so that injury to surrounding tissues can be avoided.

Preferably, the neck comprises a gate to selectively prevent or allow passage of fluid through the neck. In a closed state, the gate prevents passage of fluid from one anatomical compartment to the other. The gate may be opened and maintained in an open stated mechanically, for example by using a flow-regulating device as described below.

In a preferred embodiment, the system further comprises an intracorporeal device for regulating the flow of fluid between the two anatomical compartments. This flow-regulating device may enable the fluid flow from one compartment to the other to be interrupted or initiated, or the fluid flow rate to be adjusted. This is particularly advantageous because the present system creates fluid communication through an artificial opening through an anatomical wall and there would therefore be no natural existing mechanism to regulate the flow of fluid between anatomical compartments. For example, in the circulatory system, blood circulation is regulated by the heart muscles and existing natural openings, such as the aortic valve or mitral valves. The present invention does not rely on these natural openings and does not seek to repair defective natural openings, but instead create a new artificial blood pathway.

Preferably, the flow regulating device comprises an actuator to allow or prevent fluid flow through the intracorporeal connector. Thus, fluid communication from one anatomical compartment to the other through the connector can be activated or terminated using the actuator, preferably by opening or closing the gate of the connector neck. In a preferred embodiment, fluid communication is enabled when the flow regulation device is mechanically connected to the connector device and fluid communication is terminated when the devices are separated from each other.

Preferably, the flow regulating device comprises a pump. Thus, parameters such as fluid flow rate and/or timing of fluid flow between the anatomical compartments, and/or volume of fluid can be adjusted.

The system may further comprise means for treating or processing the fluid. In some instances, the fluid, for example blood, may be defective or require treatment. If the circulated blood is lacking in oxygen it can be oxygenated. Means for oxygen delivery can be included in the flow-regulating device, preferably by attaching an external oxygenator line to the device where oxygen can be released through trans membranous passage (membrane-oxygenation) or directly into the blood stream through microscopic openings (bubble-oxygenation).

Furthermore, the blood may be treated by delivering one or more drug compounds to the fluid or equally, one could envisage means for removing a component (such as a contaminant) of the fluid when it flows through the system according to the present invention. Such delivery and removal means could be a chemical filter, a membrane and/or one or more openings in the device attached to an externalised line for substance transport. Advantageously, the intracorporeal device for regulating the flow of fluid comprises the fluid treatment means. If required, the system may also remove oxygen and/or other gas from the fluid. Other treatments such as heating or cooling of the fluid can also be effected where required.

The fluid treatment means may enable the introduction of one or more drug compounds for treating the fluid or for delivery into one or both compartments and/or the introduction of one or more gas, for example oxygen. The flow regulating device may include a controller to adjust the treatment parameters, such as timing, concentrations and dosages. A slow release or controlled release mechanism for drug delivery is also envisaged.

Preferably, the system comprises means for securing the flow regulating means to the connector. The connector device and/or the flow regulating device may comprise one or more securing means for secured attachment to each other. The two devices may be detachably or non-detachably secured to each other. This securing means is particularly advantageous when there is a risk of the devices becoming accidentally disconnected because of anatomical movement (e.g. from the heart muscles), movement from the patient, an/or fluid flow.

Preferably, the flow regulating device is partly or wholly made of a magnetic material. For example, one or more elements of the device (e.g. casing, blade, magnetic bearing, magnetic drive etc) are made of a material with magnetic properties.

The present system is particularly advantageous when one or both anatomical compartments are compartments of the circulatory system. Compartments of the circulatory system include for example the left atrium, the right atrium, the left ventricle, the right ventricle, the aorta, the vena cava as well as arteries, veins and other compartments of the peripheral vascular system. More preferably, the system according to the present invention creates fluid communication between two adjacent compartments.

Preferably, the fluid comprises or is blood, which may be oxygenated or deoxygenated. The system according to the present invention is advantageously used as a mechanical support system, preferably as a mechanical circulatory support system, such as a ventricular assist device.

In a preferred embodiment, the flow regulating device can be arranged in a first configuration for insertion through a sheath and in a second working configuration. This is particularly advantageous as it improves the potential size (and therefore the efficiency) of the pump for percutaneous delivery which may also improve the potential for employing percutaneous magnetic drive pumps for long term use. The flow regulating device may comprise a rotatable shaft supporting at least one blade, said blade being adapted for extension in the longitudinal direction of the shaft into an insertion configuration. The blade is adapted for relaxation in the longitudinal direction of the shaft into a working configuration.

In the lateral direction of the shaft, the dimension of the blade may be greater in the working configuration than in the insertion configuration. Thus, the blade and hence the flow regulating device can easily be inserted through a sheath.

Preferably, the blade is a screw type blade. The blade may be one continuous blade and/or a serpentine type blade. Preferably, the blade is made of a resilient (memory) material so that the blade can be extended or stretched in the longitudinal direction of the shaft.

In a preferred embodiment, the system further comprises a percutaneous insertion device comprising a needle. The needle comprises a needle body, a guide wire and a puncture head. The percutaneous insertion device enables the puncture of anatomical structures, for example anatomical wall(s) separating anatomical compartments, and is particularly advantageous for the puncture of outer walls of anatomical compartments with greater tissue resistance. In addition, the insertion device enables the percutaneous insertion of a guidewire over which the various elements of the system according to the present invention, such as the intracorporeal connector device or the intracorporeal flow regulating device, can be inserted.

Preferably, the puncture head comprises a solid tip. In other words, the puncture head is not hollow like in a conventional vascular puncture-needle as this would create an unnecessarily larger incision and often will require the use of undesired force for successful puncture. Larger incisions are not desirable where dangerously high blood flows are expected. Preferably, the puncture head comprises a conical shape to allow for a smooth atraumatic puncture allowing for improved precision and control in a critical phase of the procedure.

In one type of known insertion systems, a hollow needle is used to puncture the skin. A catheter slides over the needle and the needle is removed leaving the catheter in place. A second type of known insertion system, a hollow needle is used to puncture the skin. A guide wire is inserted through the needle channel and the needle is removed leaving the guide wire in place. A catheter is then passed over the guide wire and the wire is removed, leaving the catheter in place. In the present invention, the puncture is made with the distal end of the guide wire, and in particular with the puncture head of the guide wire. This allows for a gradual, atraumatic and accurate incision to be made and this is particularly advantageous when puncturing outer walls of anatomical compartments, for example for cardiac to extra-cardiac puncture such as from one heart compartment heart into a major blood vessel.

Preferably, the dimensions of the widest cross section of the puncture head (or largest diameter in the case of a conical puncture head) are substantially the same as those of the distal end of the guide wire. In other words, the proximal end of the puncture head is flush with, or wider than, the distal end of the guide wire so as to enable a smooth, gradual and atraumatic incision. In the case where the puncture head is a conical tip, then the puncture head may be an extension of the guide wire.

The insertion device may further comprise a dilator. Preferably, the dimensions of the widest cross section of the puncture head or largest diameter in the case of a conical puncture head) are substantially the same as those of the distal end of the dilator. In other words, the proximal end of the puncture head is flush with the distal end of the dilator so as to enable a smooth, gradual and atraumatic incision. The puncture head can safely and accurately advance through the patient's anatomy.

The insertion device allows the puncture of anatomical walls and the insertion of a sheath or catheter through the patient's anatomy for subsequent introduction of percutaneous devices and the insertion device may further comprise means for guiding a sheath.

The system may be presented in the form of a kit comprising an intracorporeal connector, an intracorporeal flow regulating device and/or a percutaneous insertion device.

According to a second aspect of the invention, there is provided an intracorporeal connector as specified in any one of the preceding paragraphs.

According to a third aspect of the invention, there is provided an intracorporeal flow regulating device as specified in any one of the preceding paragraphs.

According to a fourth aspect of the invention, there is provided a percutaneous insertion device as specified in any one of the preceding paragraphs.

According to a fifth aspect of the invention, there is provided a percutaneous method for providing fluid communication between two anatomical compartments, the method comprising the steps of puncturing the wall(s) separating the compartments and inserting an intracorporeal connector through the puncture(s) for fluid communication between the two compartments.

Preferably, the puncturing step is carried out using an insertion device as specified in any one of the preceding paragraphs.

Preferably, the intracorporeal connector is a connector as specified in any one of the preceding paragraphs.

The method may further comprise the step of regulating the flow of fluid between the two anatomical compartments. Preferably, the flow of fluid is regulated using an intracorporeal flow regulating device as specified in any one of the preceding paragraphs.

The method may further comprise the step of treating the fluid. Preferably, the treatment of the fluid is carried out using the treatment means as specified in any one of the preceding paragraphs.

The method according to the present invention is particularly advantageous when one or both compartments are compartments of the circulatory system.

The present invention also concerns a percutaneous method for creating an artificial communication between two separate compartments through an anatomical wall (as opposed to a natural existing anatomical opening) comprising the step of using the percutaneous insertion device as described above, a percutaneous method for treating and/or processing a fluid comprising the step of using a flow regulating device as described above, a method for inserting an intracorporeal connector as described above, a method for inserting an intracorporeal flow regulation device as described above. Other methods relating to the present invention will be described below by way of example.

Within the context of the invention, the term "percutaneous" is used with reference to any medical procedure where access to inner organs or other tissue is done through a puncture and/or incision through the skin (and/or the vascular system) for example into the circulatory system, as opposed to an open surgery procedure. Thus, a percutaneous method involves the percutaneous delivery of elements and may involve an incision (for example with a scalpel) to enable percutaneous delivery. In a preferred embodiment, the method provides transcardiovascular delivery of one or more devices for establishing fluid communication between anatomically separate thoracic organs, after gaining access to the vascular system by a puncture or incision. The puncture or incision may be made at various sites where intravascular access is possible, for example in the groin, axilla, chest or abdomen.

BRIEF DESCRIPTION OF THE DRAWINGS

The invention will be further described with reference to the drawings and figures, in which:

FIG. 3 is a schematic representation of an intracorporeal connector according to the present invention;

FIGS. 7A to 7C are schematic representations of a percutaneous insertion device according to the present invention;

FIG. 16 is a schematic representation of a second preferred compressible flow regulating device according to the present invention in an inserted state;

FIG. 17 is a partial schematic representation of a compressible flow regulating device as shown in FIG. 15;

DETAILED DESCRIPTION

Figure 1:
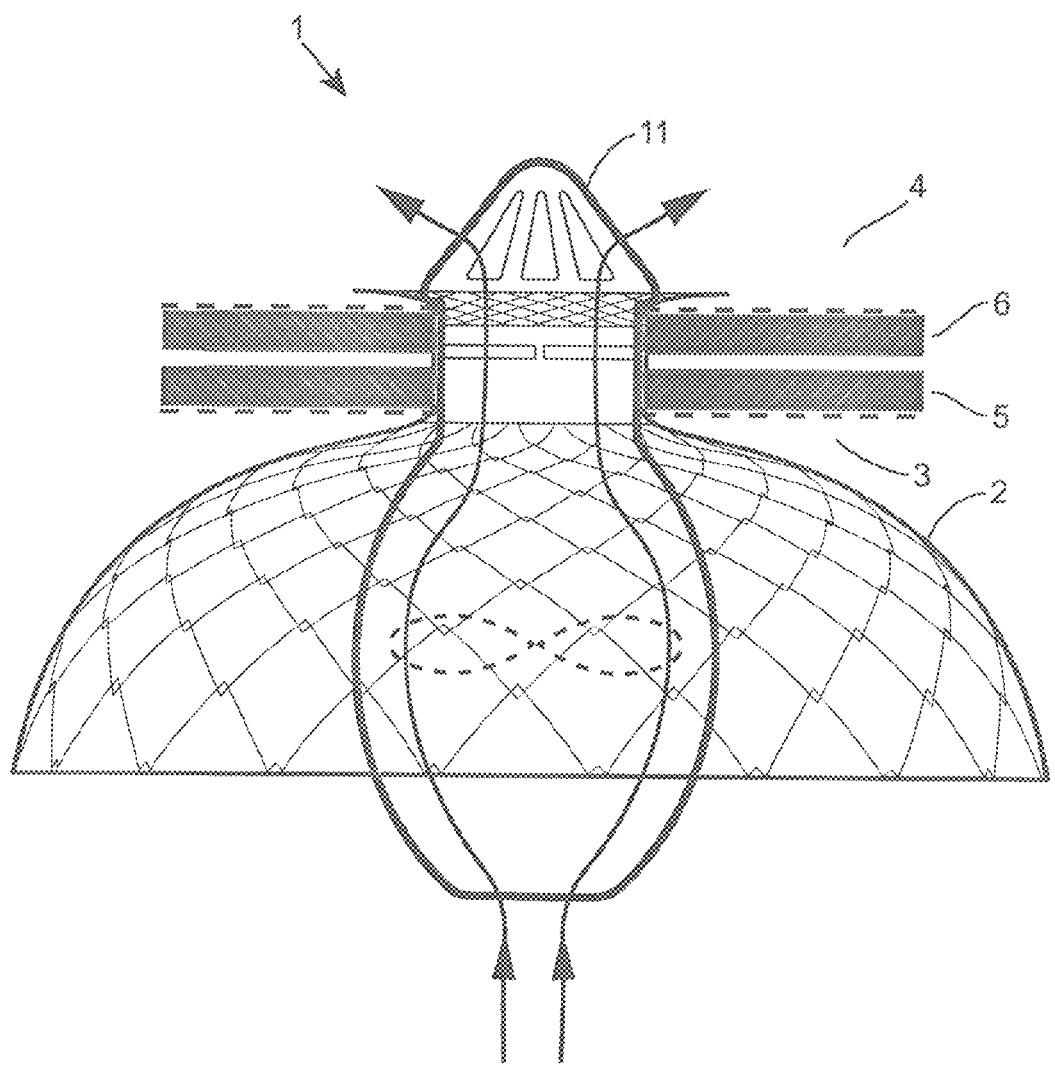
FIG. 1 is a schematic representation of an intracorporeal connector and a flow regulating device according to the present invention.
Figure 2A:
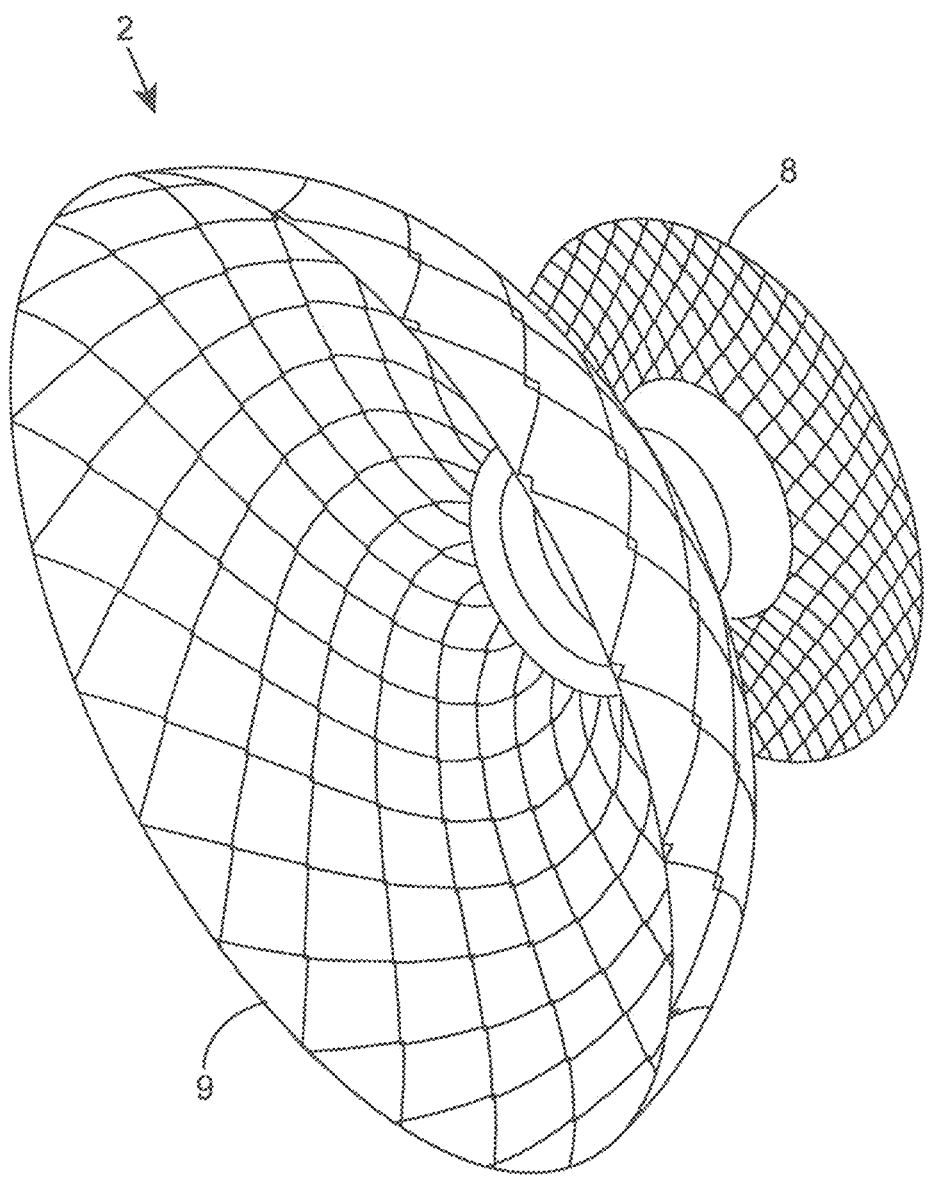
FIGS. 2A to 2C are schematic representations of an intracorporeal connector according to the present invention.
Figure 2B:
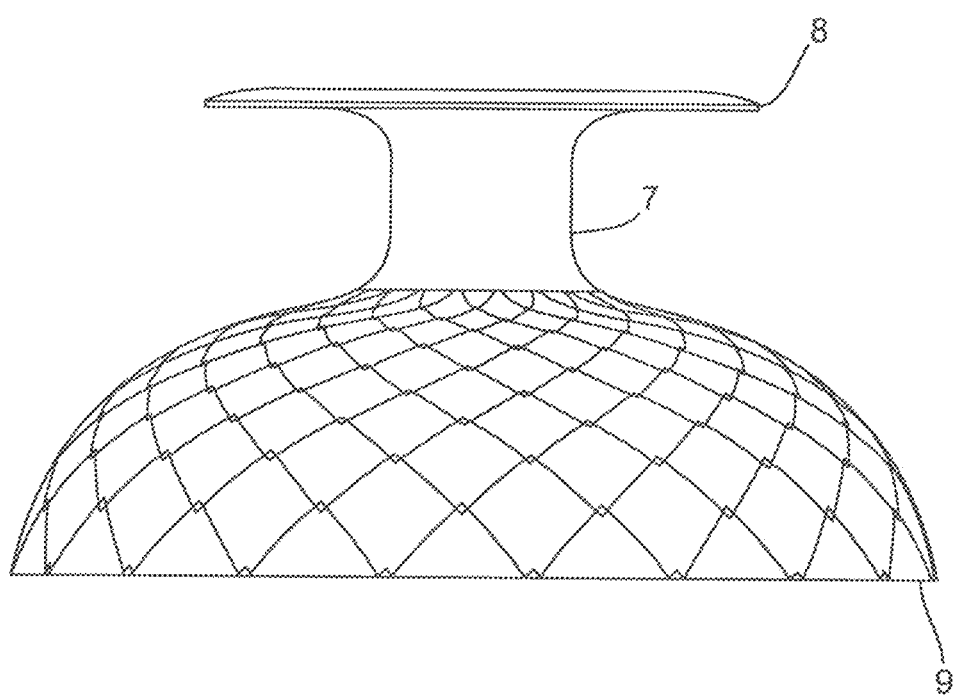
Figure 2C:
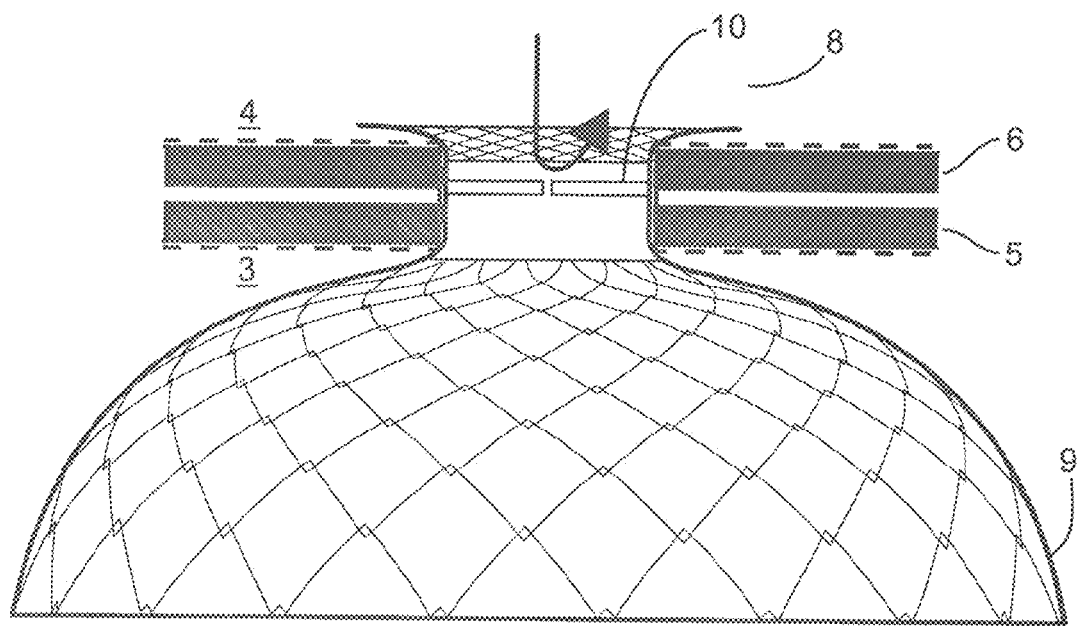

Referring to FIG. 1, there is illustrated a percutaneous system 1, in situ, comprising an intracorporeal connector 2 for fluid communication between two anatomical compartments 3,4 through at least one wall 5,6. In this illustration the first compartment is the left atrium 3 of the heart, the second compartment is the aorta 4, a first anatomical wall is the roof 5 of the left atrium 3 and a second wall is the wall 6 of the aorta 6.

An intracorporeal connector 2 according to the present invention will be described with reference to FIGS. 1 and 2A to 2C. The connector 2 comprises a waist or neck 7, and anchor 8 and a shield 9. Fluid, in this case blood, can flow across the neck 7 through a gate 10. The connector 2 is made of one or more biocompatible material and, if required, can be left in the patient after the treatment is completed.

Figure 3A:
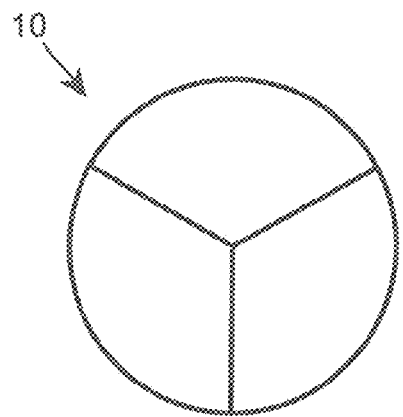
FIGS. 3A and 3B are schematic representations of gates for an intracorporeal connector according to the present invention.
Figure 3B:
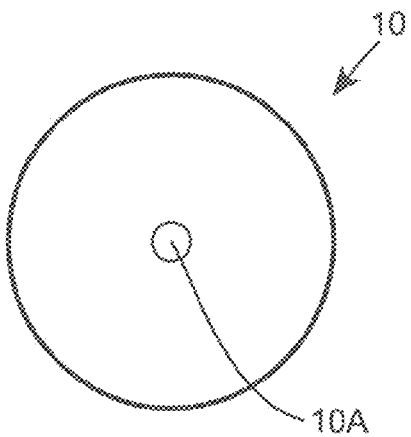

The neck 7 is typically made of a semi-flexible to substantially rigid material so that the pressure from the surrounding tissues does not compress the neck 7 and prevent fluid flow. The neck 7 comprises a biocompatible or surgical material, such as a metal or plastic material. The gate 10 is made of a resilient material (such as a plastic material or shape memory material) so that it can be in an open position allowing fluid flow or a closed position preventing fluid flow. The gate 10 retains a closed position in the absence of action from an actuator. Two examples of gate 10 are shown in FIGS. 3A and 3B. In FIG. 3A, the gate 10 is made of several portions which can fit together in a closed position and can be pushed apart to create an opening. In FIG. 3B, the gate 10 comprises an opening 10A which prevents blood flow in a closed position, but can be stretched into an open position to allow blood flow.

In this embodiment, the system 1 connects the left atrium 3 to the aorta 4, which are relatively close to each other. However, where the compartments are oddly positioned or further from each other, the dimensions and shape of the neck 7 can be modified. For example, the neck 7 may be flexible enough to bend into a suitable position or articulated.

Figure 10A:
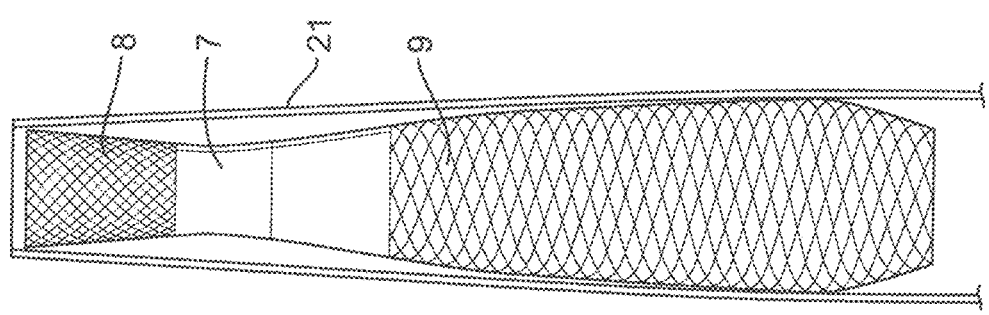
FIGS. 10A and 10B are schematic representations of an intracorporeal connector according to the present invention in a compressed state.
Figure 10B:
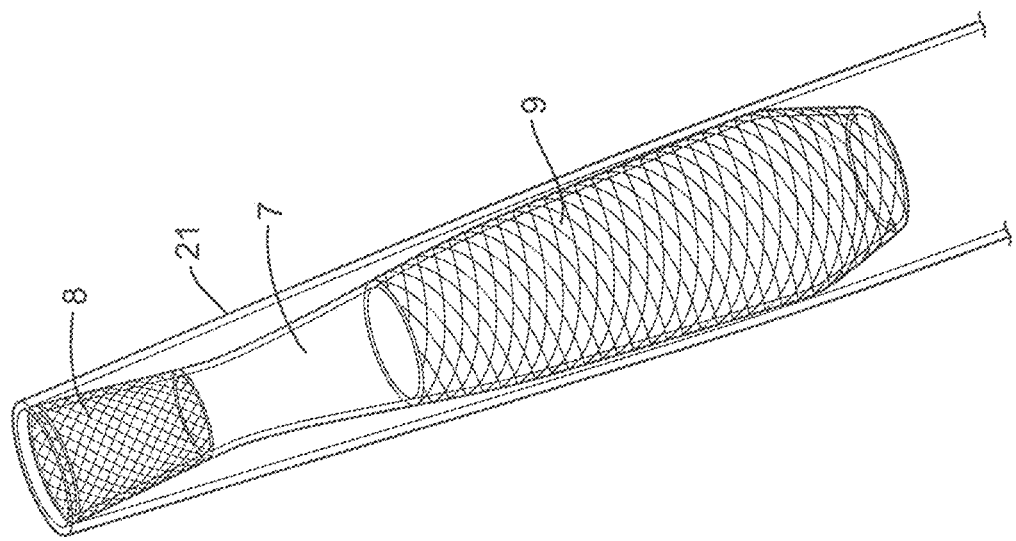

The anchor 8 extends from a first end of the neck 7. The anchor 8 is made of a resilient material, such as a shape memory material, so that it can be inserted in a folded state, as shown in FIGS. 10A and 10B and installed in an expanded state, as shown in FIGS. 1 and 2. In its folded state, the anchor 8 has a substantially cylindrical shape. In its expanded state, the anchor 8 can be deployed to prevent the connector 2 from moving within or being dislodged from the anatomical walls 5,6. In this embodiment, the anchor 8 in its expanded state is attached to and extends substantially perpendicularly from the end of the neck 7 so that it lies against and/or substantially parallel to the anatomical wall, here the aortic wall 6.

The shield 9 extends from the second end of the neck 7. The shield 9 is made of a resilient material, such as a shape memory material, so that it can be inserted in a folded state, as shown in FIGS. 10A and 10B and installed in an expanded state, as shown in FIGS. 1 and 2. The shield 9 comprises a mesh-type or grid-type material and can be made of the same material or a different material than that of the anchor 8. In its folded state, the shield 9 has a substantially cylindrical shape. In its expanded state, the shield 9 can be deployed to prevent surrounding tissues from being sucked towards and/or into the puncture through the anatomical walls 5,6. The shield 9 expands so that the surrounding tissues are not contacting the shield. This minimises the risk of injury due to suction through the mesh or rubbing against the shield. In this embodiment, the shield 9 expands into a substantially bowl-shape or umbrella-shape.

The connector 2 is designed to support the structural integrity of the anatomical walls and compartments.

A flow regulating device 11 according to the present invention will now be described with reference to FIGS. 4 and 5.

The device 11 comprises distal portion 11A, an intermediate portion 1 lB and a proximal portion 11C. In use, the distal end or tip of the distal portion 11A extends into one anatomical compartment 4 and the proximal end or tip of the proximal portion 11C extends into the second anatomical compartment. The intermediary portion 11C sits partially or completely in the neck 7 of the connector 2. Within the context of the invention, the term "distal" refers to the position closest to the patient and the term "proximal" to the position closest to the medical practitioner in the direction of insertion. In other words, the distal end of a device is inserted first and its proximal end is inserted last.

The device 11 comprises a channel (now shown) for blood passage through from the proximal portion 11C to the distal portion 11A of the device 11. The proximal end comprises one or more openings 12 to allow blood to enter the device 11, and the distal end comprises one or more openings 13 to allow blood to exit the device 11. The distal end of the device 11 is rounded to minimise trauma and pointed for ease of insertion.

Figure 5A:
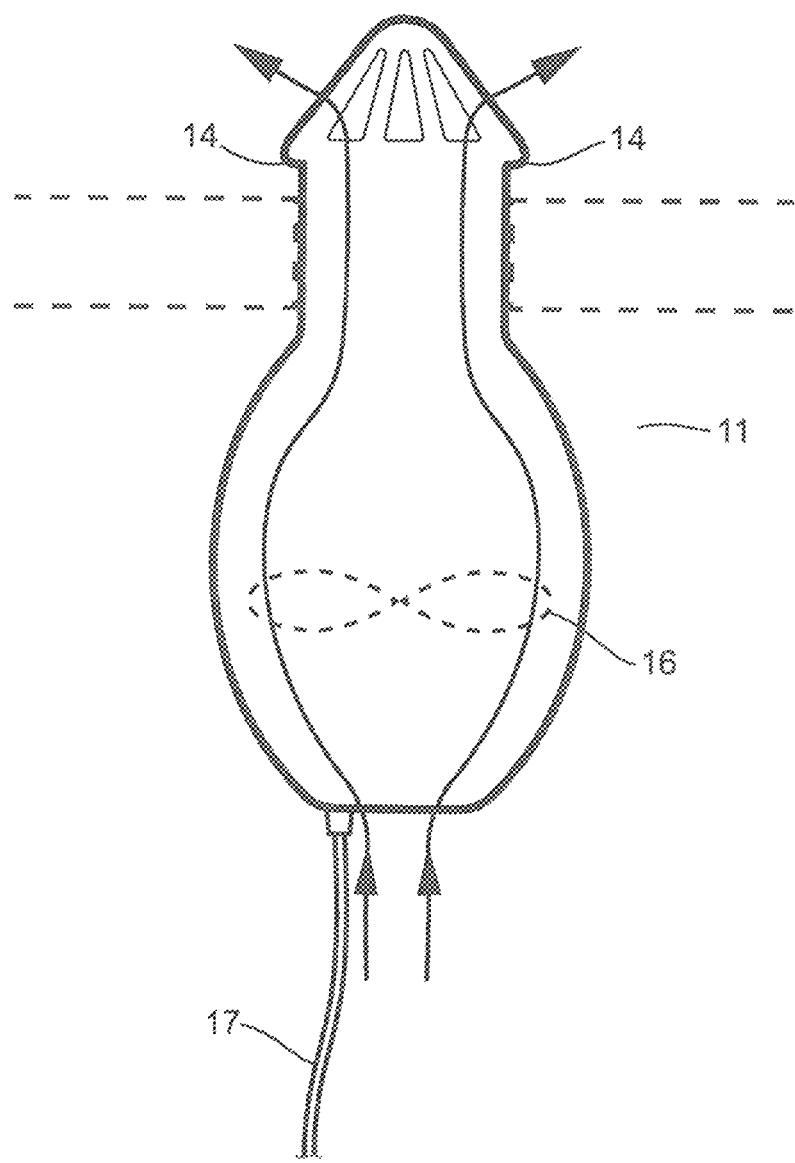
FIGS. 5A to 5C are schematic representations of an intracorporeal connector according to the present invention.
Figure 5B:
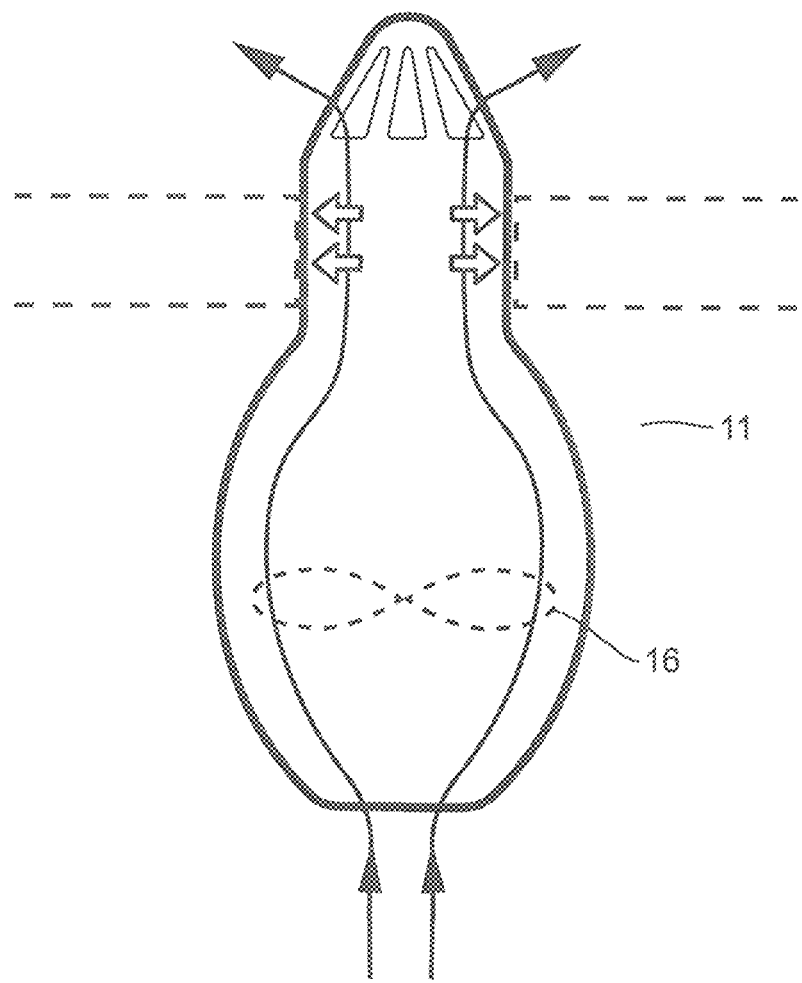
Figure 5C:
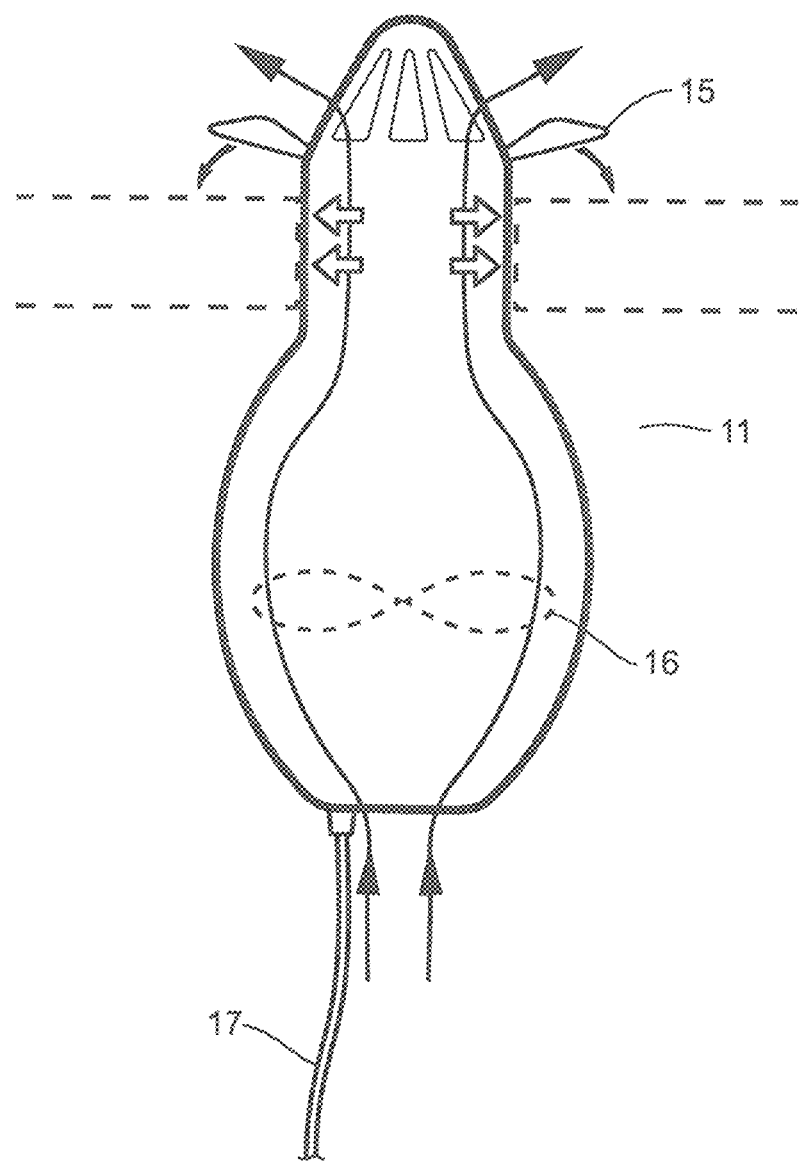

The flow regulating device 11 comprises means for securing the device 11 to the connector 2 and examples of such securing means are illustrated in FIGS. 5A to 5B. In FIG. 5A, the distal portion of the device 11 comprises one or more ribs 14 or tabs which prevent the device 11 from moving against the flow of fluid. In FIG. 5B, the intermediary portion 11B is partially or wholly made of a resilient or expandable material, which maintains the device 11 in place. The outer surface of the intermediary portion 1 lB can be modified so that it provides a better grip onto the connector neck's inner surface. In FIG. 5C, the distal portion 11A of the device 11 comprises flaps 15 or tabs which can be expanded to prevent the device 11 from moving against the flow of fluid or folded during the insertion procedure.

Another example of securing means is embodied by the gate 10. During the insertion procedure, the distal tip of the device 11 is pushed through and opens the gate 10, and, in its inserted position, the intermediary portion 11C sits partially or completely in the neck 7 of the connector 2, through the gate 10. Thus, the gate material resiliently closes around the distal portion 11B of the device 11 and secure the device 11 to the connector 2. In this description of the insertion procedure, the distal portion 11A or distal end of the distal portion 11A of the device 11 acts as an actuator to the connector 2, by opening the gate 10 and allowing blood to flow from the left atrium to the aorta.

The flow regulating device 11 comprises an internal pump 16. The pumping parameters can be adjusted by an intracorporeal or extracorporeal controller (not shown). In the case of an extracorporeal controller, wireless control is preferred. Current can be fed to the pump 16 through an electrical lead 17 or the device 11 can contain an internal battery. In the case of a chargeable battery, charging mechanisms which do no involve the insertion of further devices into the patient are preferred, for example, a magnetic charging mechanism. If the battery cannot be recharged, then the device 11 can be removed and replaced or discarded after use. The electrical lead 17 or other tubing may be used as a pull string to remove the device 11 from the patient after use or a dedicated pull string may be added.

If the fluid pumped from one compartment 3 requires treatment or processing before being delivered into the second compartment 4, suitable means (not shown) can be incorporated into the device 11. For example, a drug delivery device can contact the blood flowing through the device 11 with one or more drugs; or the blood can be oxygenated before exiting the device 11 using an oxygenating device or membrane. In the case of drug delivery, the device 11 incorporates a drug reservoir or be connected to an external drug reservoir. A slow- or controlled-release mechanism is also envisaged. The system 1 according to the present invention could also be regarded as an intracorporeal drug delivery system, in which a drug is delivered into a target compartment, with or without blood flow.

The flow regulating device 11 is self contained so that all the elements, including the pump 16, drug delivery or oxygenation devices, as required, are incorporated in the casing of the flow regulating device 11.

A preferred flow regulating device 11 for use in the present invention is described with reference to FIGS. 16 to 19. This device 11 is a variation of the device as described above and can comprise any feature relating to the device 11 as described in the preceding paragraphs.

The flow regulating device 11 comprises a distal portion 11A, an intermediate portion 11B and a proximal portion 11C. The proximal portion 11C forms a casing partially or wholly surrounding the pump 16. The proximal portion 11C further comprises a detachable base 11D. The base 11D can be attached by rotation, for example by screw or bayonet means. This detachable base 11D comprises one or more openings 27 so that fluid can flow into the base openings 27 from a first anatomical compartment, through the device 11 and exit through openings 13 at the distal portion 11A of the device 11 into a second anatomical compartment.

The base 11D comprises a rotatable shaft 16A supporting at least one blade 16B. The blade 16B is a screw type blade extending from the shaft 16A. The proximal end of the blade may be extend from the shaft 16A. The distal end of the blade 16B may be attached or not to the distal end of the proximal portion 11C of the device 11 or the proximal end of the intermediate portion 11B of the device 11. The screw blade 16B is arranged and constructed such that it can be extended or stretched in the longitudinal direction of the shaft 16A for ease of insertion through a working sheath 21. In this extended configuration, the screw blade 16B is stretched longitudinally so that the overall diameter of the blade 16B is smaller than in the relaxed configuration. The blade 16B reverts to its original relaxed configuration, i.e. its working configuration, as it exits the sheath 21. In its working configuration, the overall diameter of the blade 16B is greater than in the stretched position. Thus, in the stretched configuration, the screw blade 16B can easily be inserted through a sheath 21 and in the working configuration, the size of the blade 16B is maximised for optimum capacity and efficiency. This also means that a blade 16B with a greater number of thread forms per unit length (and therefore greater efficiency) can be used. Any part of the device 11, in particular, the proximal portion 11C of the device 11 and/or blade 16B, can be made of a resilient (or shape memory) material, which may be the same or different. In a preferred embodiment, the extendable pump is surrounded by a proximal portion 11C of the device 11, and the proximal portion 11C is made of a resilient material such that it can be compressed to fit into a sheath and subsequently deployed use. In this embodiment, the base 11D is preferably made of a rigid material.

The base 11D can comprise a compartment (not shown) for including a pump motor, other elements required for the pump to function, fluid treatment and/or processing means as described above. Alternatively, the base 11D or proximal portion 11C may comprise one or more ridges for drug and/or oxygen delivery. The ridges can for example be disposed around the shaft 16A. Any connection 17 between the device 11 and outside the patient's body can be attached to the base 11D.

The principle of deployable percutaneous elements, such as expandable connectors and flow regulating devices, by-passes the current need for miniaturisation. In other words, instead of reducing the size (and therefore compromising capacity and efficiency) of the elements, full size elements can be inserted into the patient's vascular system through small incisions in a folded or compressed state, deployed at the correct location and subsequently removed from the patient in a folded or compressed state. This paves the way for a more versatile system in terms of size and shapes and children in particular would benefit greatly. This also means that, not only subcutaneous drivelines (similar to those used in connection with pacemakers) can be used, but also external drivelines and deployable elements can be inserted through the venous system. Thus, if major arteries can be avoided, the risk of infection and heavy bleeding is minimised.

Figure 6B:
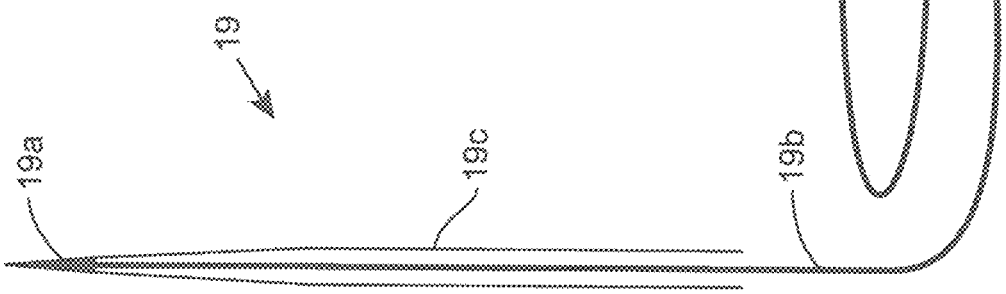
FIGS. 6A to 6C are schematic representations of a percutaneous insertion device according to the present invention.
Figure 6A:
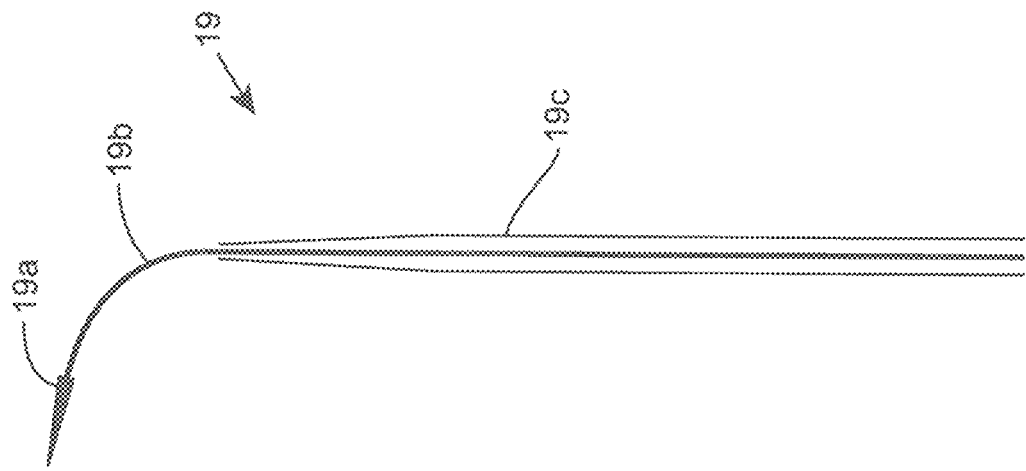
Figure 6C:
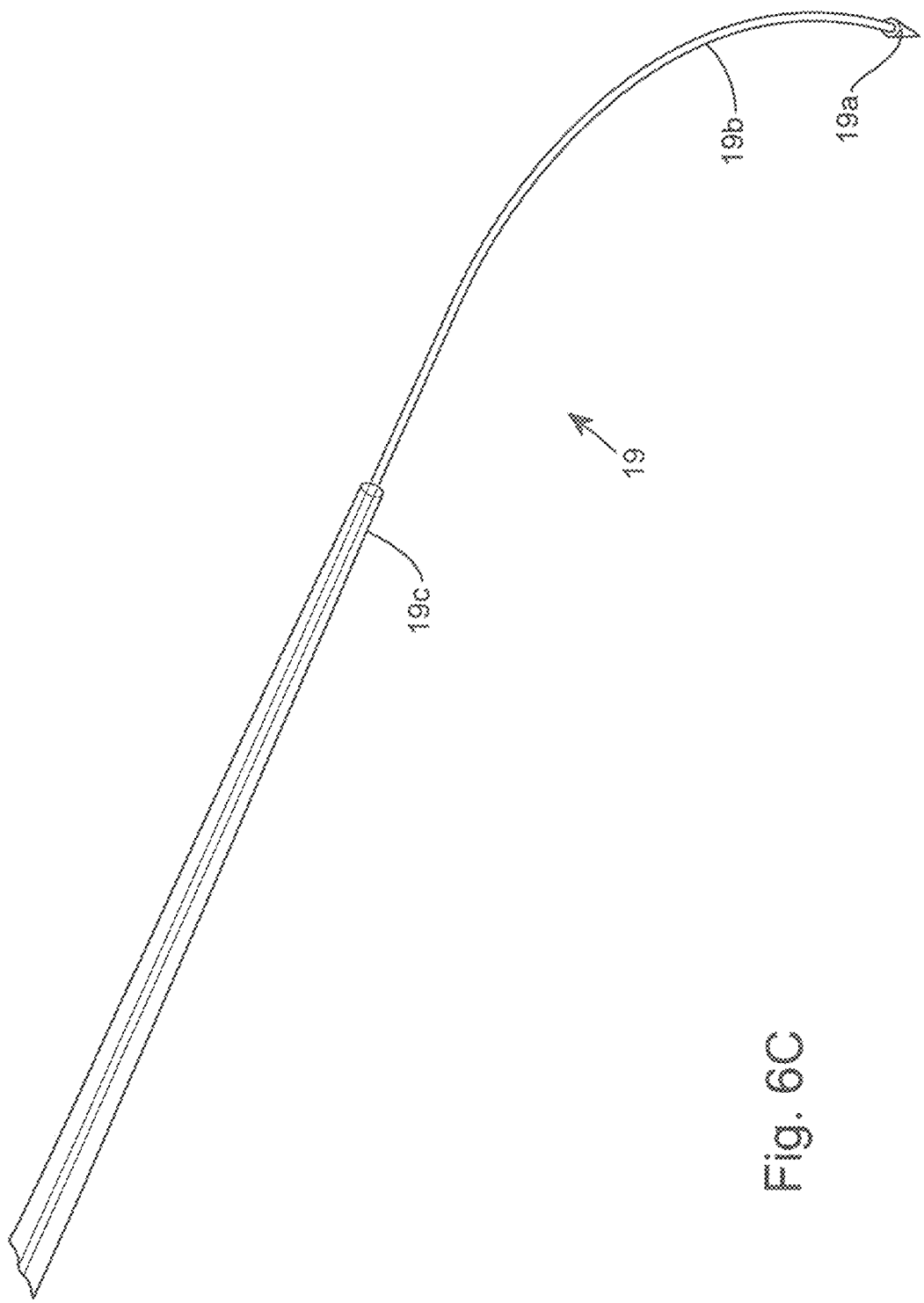
Figure 8:
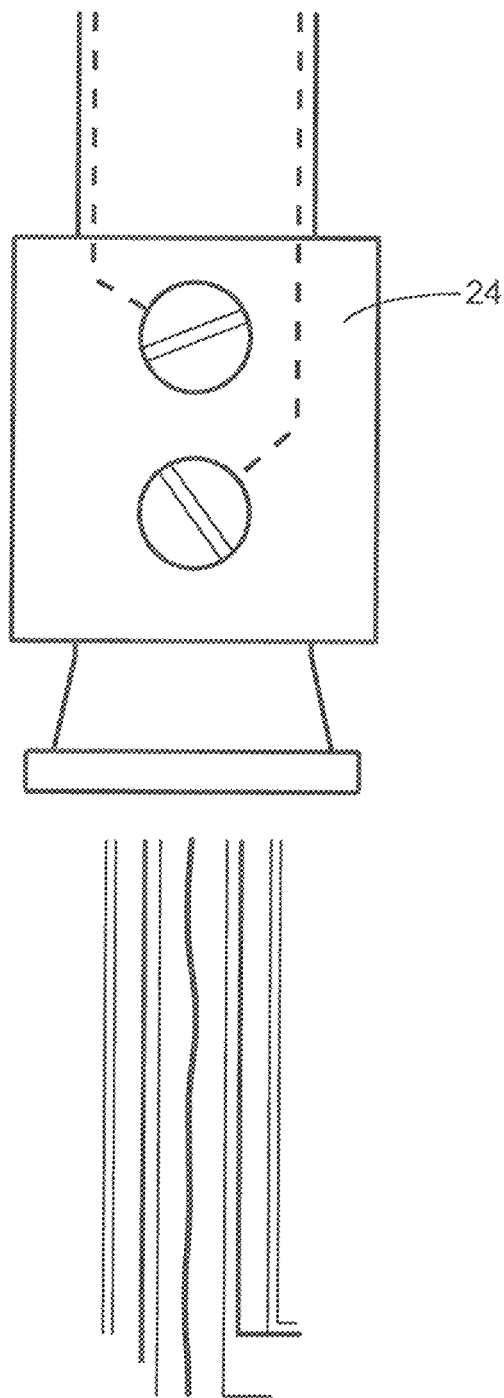
FIG. 8 is a schematic representation of a steering mechanism for a percutaneous insertion device according to the present invention.

A percutaneous insertion device 18 according to the present invention will now be described with reference to FIGS. 6 to 8.

The percutaneous insertion device 18 comprises a needle 19. The needle 19 comprises a puncture head 19a at its distal end, a guide wire 19b and a needle body 19c. The insertion device further comprises a dilator 20, an working sheath 21, a support sheath 22 and an outer casing 23. The insertion device 18 is used to insert any element which may be required for the method according to the present invention. As will be described in more detail below, the needle 19 and in particular the puncture head 19a is used to puncture one or more anatomical walls; the guide wire 19b to direct the elements during insertion; the dilator 20 to stretch punctures made by the puncture head 19a; the working sheath 21 and the support sheath 22 to form a safe passageway for inserting the elements of the system 1.

In this embodiment, the puncture head 19a is connected to the distal end of the guide wire 19b for example by welding. The puncture head 19a has a solid tip, i.e. devoid of a hollow channel as observed in standard insertion or injection needles. The puncture head 19a is conically shaped and the diameter at the base of the conical puncture head 19a is larger than that of the guide wire 19b. The guide wire 19a is slidable through a needle body 19c. The diameter at the base of the conical puncture head 19a is substantially equal to that of the distal end of the needle body 19c so as to create a flush, smooth transition.

In an alternative embodiment (not shown), the diameter at the base of the conical puncture head 19a is substantially the same as that of the guide wire 19b so that the guide wire 19b is a tapered guide wire. In this alternative embodiment, the puncture head 19a and the guide wire 19b may be integrally formed. A diameter of the guide wire 19b is substantially equal to that of the distal end of the needle body so as to create a flush, smooth transition; although in this case, the needle body 19c may not be required as the tapered guide wire 19b can act as a needle.

The use of a puncture head 19a at the distal end of the guide wire 19b allows the insertion device 18 to act as an atraumatic and accurate puncture device. These relative dimensions of the puncture head 19a, the guide wire 19b and the needle body 19c enable the size of the puncture to be gradually and gently increased.

The guide wire 19a comprises three sections of different rigidity, namely a distal portion of relatively rigid material, an intermediate portion of flexible material and a proximal portion of relatively rigid material. These differences in rigidity enable the manipulation and guiding of the guide wire through the patient's anatomy.

As will be described below in more details, the insertion element 18 enables the creation of a safe pathway for the insertion, installation and removal of the various elements of the system 1. More specifically, the insertion device 18 according to the present invention is particularly advantageous for the puncture of an anatomical wall, such as an outer wall of an anatomical compartment which has a greater tissue resistance. The insertions device 18 also enables a particularly accurate and small incision to be created, which is crucial in incisions involving high pressure blood flow. A preferred use of the insertion element 18 is for the puncture of outer walls of internal organs, for example for an extra-cardiac puncture.

A method according to the present invention will now be described by way of example with reference to a left atrium—aorta connection.

Figure 9:
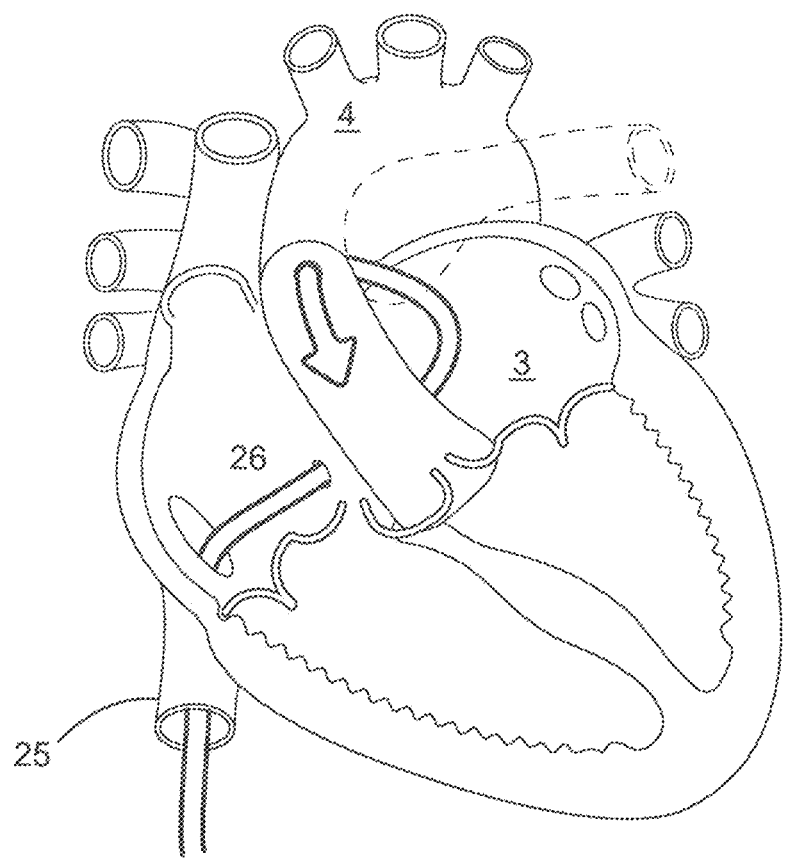
FIG. 9 is an illustration of an insertion route in a method according to the present invention.

The first step is the insertion of a guide wire, which can be carried out by means known in the art. A needle carrying a guide wire is placed on the groin area of the patient, adjacent the femoral artery. Pressure is applied so that the patient's skin is punctured by the tip of the needle and pushed through the skin and tissues into the femoral artery. Once in place, the guide wire is advanced along the femoral artery and up the inferior vena cava 25. With reference to FIG. 9, the guide wire exists the inferior vena cava 25 and enters the right atrium 26. The septal puncture between the right and left atrium can also be carried out by means known in the art. A guide wire now extends from outside the patient, into the femoral artery through the skin puncture, the inferior vena cava 25, the right atrium 26, the atrial septum and the left atrium 3 lodged preferably in superior left pulmonary vein. Next, a large and steerable support sheath can be deployed into the left atrium over the wire to facilitate the final steps of the procedure. The skin puncture and/or septal puncture could equally be carried out using the insertion device 18 according to the present invention, although the insertion device 18 is most advantageous when performing an extra cardiac puncture as described below.

The second step is insertion and installation of the insertion device 18 according to the present invention. The needle 19 is inserted through the groin preferably through a dedicated support sheath as described above and advanced along the same path as described above. The guide wire 19*b* comprises a relatively flexible (distal) portion adjacent to the puncture head before a more rigid proximal portion, so that as the guide wire 19*b* folds upon itself at the flexible portion, thereby forming a U-shape. The flexible portion now advances first, followed by the rigid proximal portion. Thus, the guide wire 19*b* can be moved atraumatically through the delivery sheath or alternatively, through the patient's blood vessels. The guide wire 19*b* can be straightened when required by gently pulling the proximal end and repositioning the distal portion at its front most position. The puncture head 19*a* is pulled back towards the distal end of the needle body 19*c*. Inside the vasculature, the needle 19 is preceded or followed by the support sheath 22. The support sheath 22 can be manipulated and directions controlled using a guiding means as illustrated in FIG. 8.

The third step is the extra-cardiac puncture of the left atrium using an insertion device 18 according to the present invention. The distal end of the support sheath 22 is placed against the roof of the left atrium 3 ready for puncture. The conical puncture head 19*b* is pushed against the wall so as to create an incision. This conical shape enables the medical professional to create a small and accurate extra-cardiac incision in a smooth and atraumatic manner. The support sheath 22 placed against the roof of the left atrium provides further support during this first puncture step. The puncture head 19*a* and needle body 19*c* are advanced through the incision towards the aortic wall. The support sheath 22 can be used to push the wall of the left atrium against the aortic wall and hold both walls together to assist puncture of the aortic wall. Once the aortic wall is pierced, the dilator 20 can stretch both punctures to facilitate the insertion of the working sheath 21. The needle body 19*c* and the dilator 20 can be removed to leave the guide wire 19*b* and working sheath 21 in place in the aorta 4. The guidewire 19*b* with puncture head 19*a* anchors the working sheath 21 in place and prevents the sheath 21 from becoming accidentally dislodged. The support sheath 22 can remain in the left atrium 3.

Figure 11:
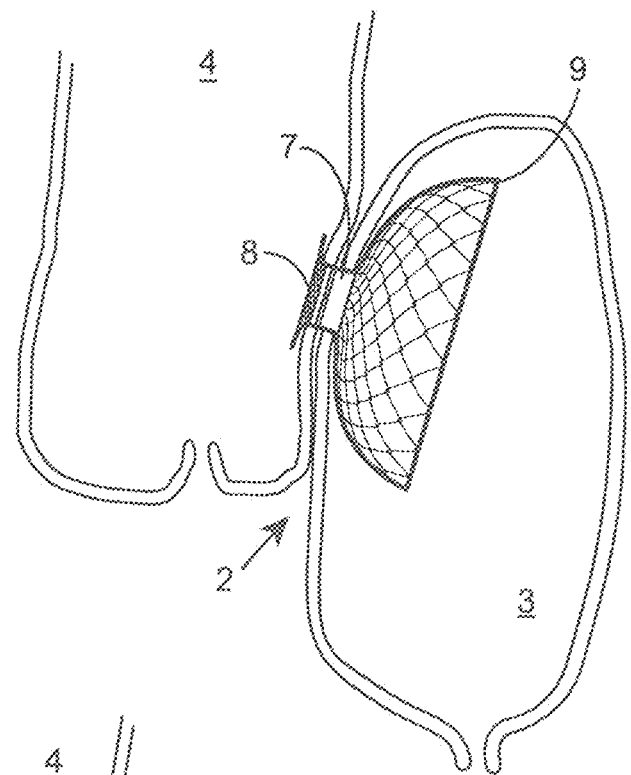
FIG. 11 is a schematic representation of an intracorporeal connector according to the present invention in situ.

The fourth step is the insertion of an intracorporeal connector 2 according to the present invention. With reference to FIGS. 10A and 10B, the intracorporeal connector 2 is inserted in a folded or compressed state into working sheath 21 along the guide wire 19*b*. When the connector 2 reaches the roof of the left atrium, it is pushed along the guide wire 19*b*, through the incision in the anatomical walls 5,6 until the neck 7 is correctly positioned across the anatomical walls 5,6 and the anchor 8 and shield 9 are deployed on either side of the walls 5, 6, in the aorta 4 and the left atrium 3, respectively (FIG. 11). The connector 2 gradually expands at it exits the distal end of the working sheath 21.

Figure 4A:
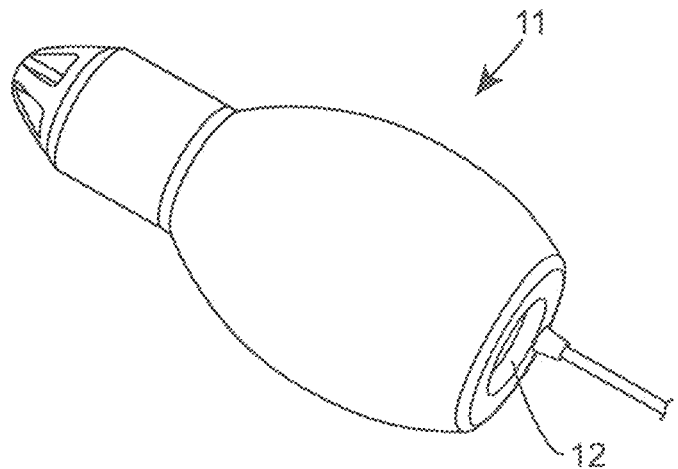
FIGS. 4A and 4B are schematic representations of a flow regulating device according to the present invention.
Figure 4B:
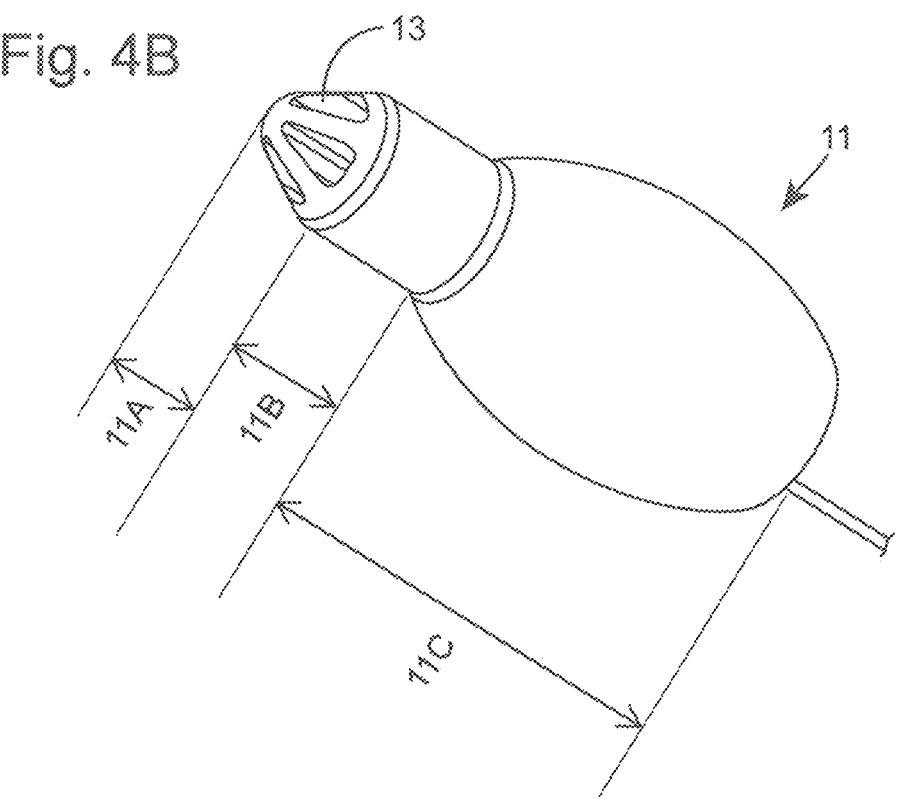
Figure 12:
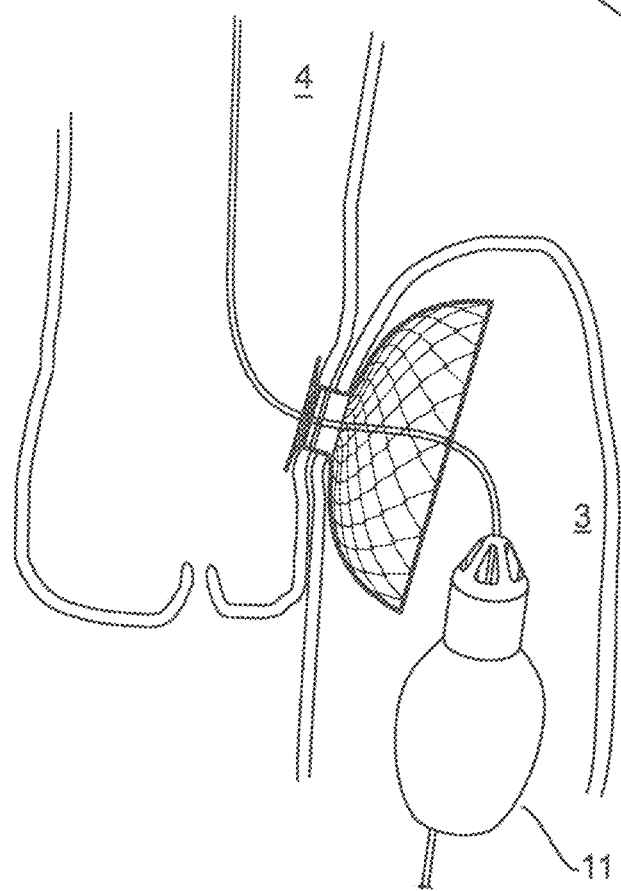
FIG. 12 is an illustration of a flow regulating device according to the present invention during the insertion process.
Figure 13:
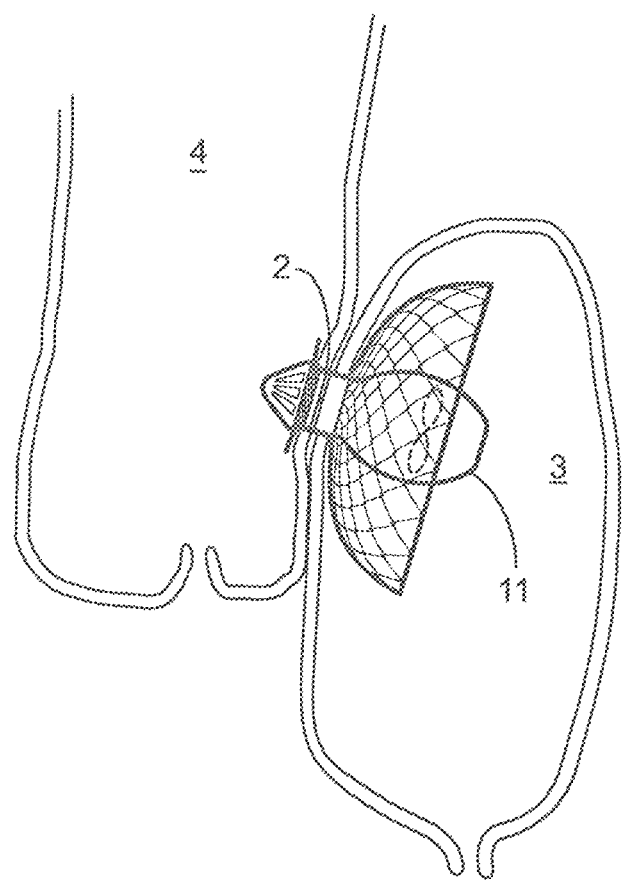
FIG. 13 is a schematic representation of a system according to the present invention in situ.
Figure 14:
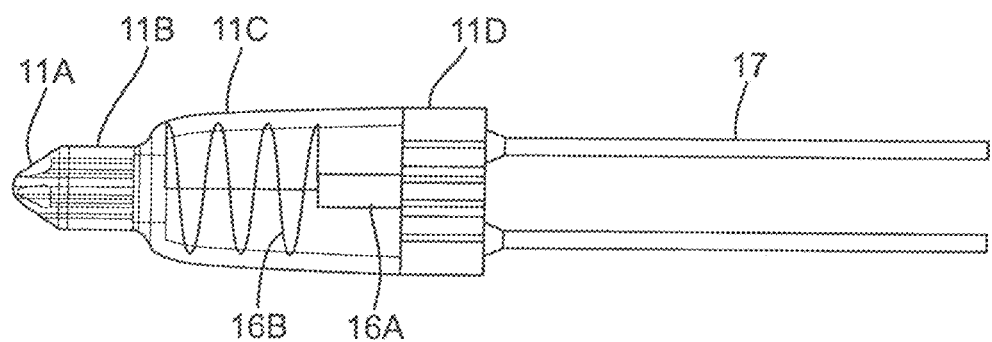
FIGS. 14 and 15 are schematic representations of a first preferred flow regulating device according to the present invention in an inserted state.
Figure 15:
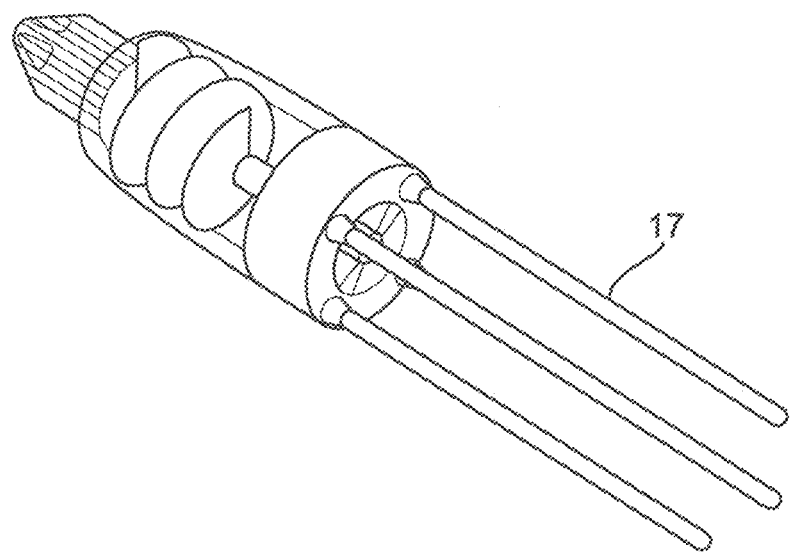
Figure 18:
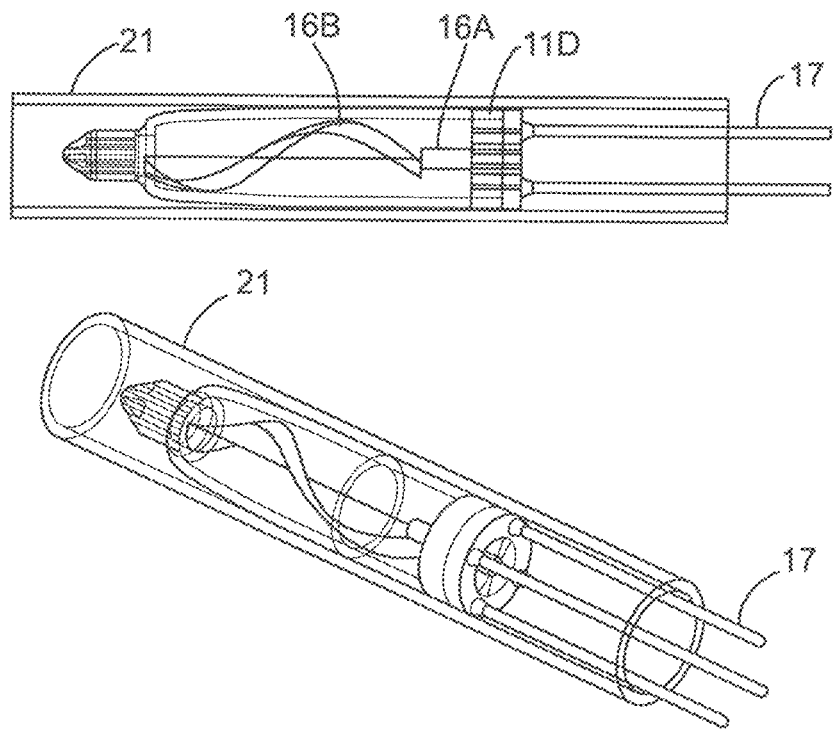
FIG. 18 is a schematic representation of the compressible flow regulating device as shown in FIG. 16 during insertion.
Figure 19:
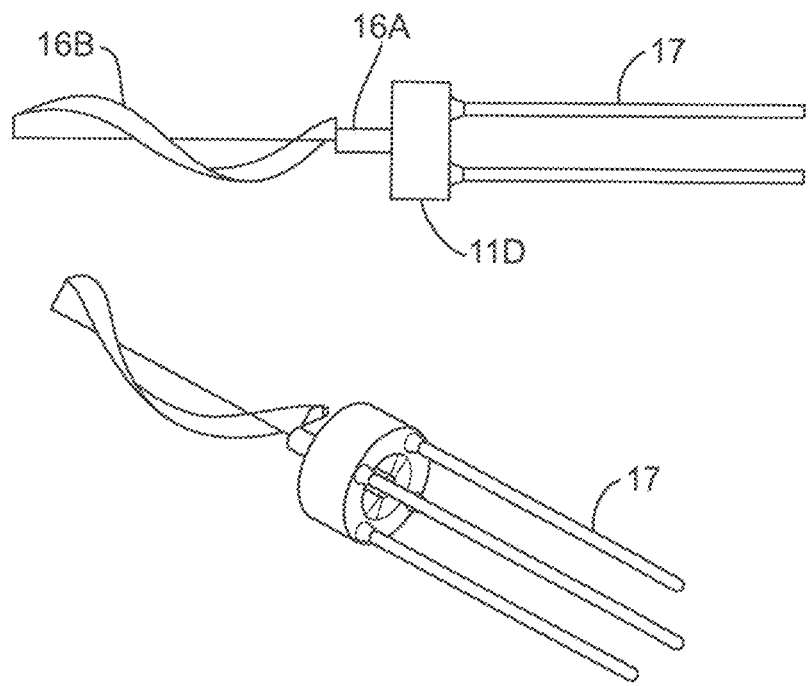
FIG. 19 is a partial schematic representation of the compressible flow regulating device as shown in FIG. 18.

The fifth step is the insertion of an intracorporeal flow regulating device 11 as shown in FIG. 4 or 15 according to the present invention. With reference to FIG. 12, the intracorporeal flow regulating device 11 is inserted and advanced through the sheath 21 and along the guide wire 19*b* until it reaches the connector 2. The distal portion 11A and more particularly the distal tip of the connector 2 acts as an actuator which opens the gate 10 in the neck 7 of the connector 7 by stretching the opening 10A of the gate 10. The intermediate portion 11B of the flow regulating device 11 sits in the neck 7 of the connector 2 and is securely positioned due to the pressure of the resilient material of the gate 10 and by ribs 14. Unless further required, the working sheath 21 can now be removed.

In the case of a compressible/expandable flow regulating device as shown in FIGS. 16 to 19, the base 11D of device 11 is detached from the proximal portion 11C and the blade 16B is stretched to its extended position. For example, the base 11D is rotated or unscrewed so that simultaneously, the base 11D is detached from proximal portion 11C and the blade 16B is extended. The device 11 is advanced to the distal end of the sheath 21 and the distal portion 11A of the device 11 suitably positioned ready to actuate gate 10. The base 11D is re-attached to the proximal portion 11C of the device 11, for example by rotating of screwing, so that the blade 16B relaxes into its working configuration. The distal portion 11A of the flow regulating device 11 can now be pushed through the gate 10 to allow fluid flow.

The insertion and installation procedures described above can be facilitated by visualisation techniques such as X-ray, fluoroscopy, echocardiography, ultrasound techniques.

The pump 16 is started and blood flow between the left atrium 3 and the aorta 4 can be adjusted. The blood flows from the left atrium 3 into the proximal end of the device 11, through the device and exits through the apertures 13 at the distal end of the device 11 into the aorta 4. Blood flow, timing of blood flow, temperature and other parameters can be controlled and adjusted. Similarly, drugs and/or oxygen can be added and/or contaminants removed from the blood as it passes through the device 11. As the blood is sucked into the device 11, surrounding tissues are prevented from hindering the blood passage by the shield 9. The blood flow has a tendency of pushing the device 11 backwards into the left atrium but the device 11 is immobilised by the securing means as described above.

The flow regulating device 11 may be removed from the patient when the treatment is completed, if charging or replacing is required. Upon removing the device 11, the gate 11 closes and blood flow is halted and the connector 2 can remain in place or be removed.

From the above description, it can be seen that the present invention constitutes a novel alternative to existing percutaneous procedures.

Although the present invention has been described with respect to a left atrium to aorta procedure, the system and method can also be applied to other delivery sites including, but not limited to, right atrium—aorta, vena cava—pulmonary artery, vena cava—aorta. Thus, the present invention can be broadly applied for example as left ventricular assist devices (LVAD), right ventricular assist devices (RVAD) or biventricular assist devices (BiVAD), for cardiopulmonary support (CPS) or for intra-corporeal membrane oxygenation (ICMO) or bubble oxygenation, for the treatment of other organs with pressure issues (e.g. gastric or neurological procedures). The present invention is versatile and a wide variety of applications can therefore be envisaged.

The present percutaneous procedure requires limited mechanical apparatus and devices and offers a simple as well as safer and cheaper alternative to existing procedures. All the elements are inserted and implanted percutaneously so that there is no need for invasive and traumatic open surgery. Furthermore, the devices described herein can be easily be applied to paediatric treatments.

It is important to note that the present invention relies on an artificially created fluid pathway. Cardiopulmonary or circulatory collapse and heart failure can be the result of a variety of acquired or natural conditions and can affect different anatomical parts of the heart and circulatory and respiratory system. Existing procedures often seek to repair or replace the existing defective anatomical parts. The present invention provides a procedure which is more forgiving in that it relies on artificially created pathways which can by-pass the defective portion of the circulatory system and allow for use of novel treatment principles and technologies compared with current treatments This system is a safe, stable and predictable structure for the delivery of improved therapeutic instruments from one compartment to another, through shorter and more beneficial routes.

The invention claimed is:

1. A percutaneous method for providing fluid communication between two anatomical compartments through at least one anatomical wall, the method comprising the steps of:
   puncturing at least two intracorporeal anatomical walls separating the compartments, comprising pushing one anatomical wall in contact with another anatomical wall using a support sheath, and
   inserting an intracorporeal connector through punctures created during the puncturing step for fluid communication between the two compartments, wherein said intracorporeal connector comprises a neck for fluid passage for one compartment to the other and means for preventing tissue from hindering fluid passage through the neck, said intracorporeal connector being configured to intracorporeally receive an intracorporeal flow regulating device,
   further comprising regulating the flow of fluid between the two anatomical compartments using the intracorporeal flow regulating device,
   wherein the flow regulating device comprises at least a pump or an actuator.

2. The method according to claim 1, wherein the puncturing step is carried out using a percutaneous insertion device comprising a needle, said needle comprising a needle body, a guide wire and a puncture head.

3. The method according to claim 1, further comprising a step of treating the fluid.

4. The method according to claim 3, wherein step of treating the fluid comprises one or more steps of:
   delivering one or more drug compounds to the fluid,
   removing a component of the fluid,
   oxygenating the fluid,
   heating the fluid, or
   cooling the fluid.

5. The method according to claim 1, wherein one or both compartments are compartments of the circulatory system.

6. The method according to claim 1, wherein the means for preventing tissue from hindering fluid passage through the neck comprises an expandable shield extending from a second end of the neck.

7. The method according to claim 6, wherein the shield deploys upon exiting a sheath.

8. The method according to claim 1, wherein connector comprises means for securing the neck across the anatomical wall.

9. The method according to claim 8, wherein the means for securing the neck across the anatomical wall comprises an expandable anchor extending from a first end of the neck.

10. The method according to claim 1, comprising the step of allowing fluid communication through the connector by mechanically connecting the flow regulating device to the connector.

11. The method according to claim 10, wherein fluid communication is terminated when the flow regulating device is disconnected from the connector.

12. The method according to claim 1, comprising the step of providing fluid communication through an extra-cardiac passageway.

* * * * *